United States Patent [19]

Kitahara et al.

[11] Patent Number: 5,079,331
[45] Date of Patent: Jan. 7, 1992

[54] HEAT-RESISTANT EPOXY RESIN COMPOSITION BASED ON 2-(4-HYDROXYPHENYL)-2-(4-MALEIMIDO-PHENYL)PROPANE

[75] Inventors: Mikio Kitahara; Koichi Machida; Takayuki Kubo; Motoyuki Torikai, all of Yokohama; Koutarou Asahina, Kamakura; Yoshimitsu Tanabe, Yokohama; Keizaburo Yamaguchi, Chiba; Akihiro Yamaguchi, Kamakura, all of Japan

[73] Assignee: Mitsui Toatsu Chemical, Inc., Tokyo, Japan

[21] Appl. No.: 527,267

[22] Filed: May 23, 1990

[30] Foreign Application Priority Data

May 30, 1989 [JP] Japan ................. 1-134584

[51] Int. Cl.⁵ .............................................. C08G 59/40
[52] U.S. Cl. .............................. 528/96; 525/502; 548/547; 548/549
[58] Field of Search .................... 528/96; 525/502; 548/547, 549

[56] References Cited

U.S. PATENT DOCUMENTS 4,632,972 12/1986 Hefner et al. ................. 528/96
4,760,105 7/1988 Fuller et al. ................. 528/96 X

OTHER PUBLICATIONS

Chemical Abstracts 97, 164029v (1982).
Chemical Abstracts 97, 163988v (1982).
Chemical Abstracts 109, 74044h (1988).
Chemical Abstracts 94, 140615v (1981).

*Primary Examiner*—John Kight, III
*Assistant Examiner*—Frederick Krass
*Attorney, Agent, or Firm*—Burns, Doane, Swecker & Mathis

[57] ABSTRACT

Heat-resistant epoxy resin composition obtained by incorporation of 2-(4-hydroxyphenyl)-2-(4-maleimidophenyl)propane in a resin composition consisting esssentially of epoxy resin and an epoxy hardener is disclosed.

12 Claims, No Drawings

HEAT-RESISTANT EPOXY RESIN COMPOSITION BASED ON 2-(4-HYDROXYPHENYL)-2-(4-MALEIMIDO-PHENYL)PROPANE

BACKGROUND OF THE INVENTION

1. Field of the Invention

The present invention relates to an epoxy resin composition which is excellent in heat-resistance and which can be used for insulation materials and laminate materials for electric and electronic parts, and particularly for sealing semiconductors.

2. Description of the Prior Art

The fields of electric equipment and electronic parts have the tendency to use high density mounting and multifunctionality. Accordingly, for insulation materials and laminate materials to be used in these fields, and particularly for sealing semiconductors, it is strongly desired to develop heat-resistant resin compositions capable of withstanding heat generation in the mounting step or in use. Technical innovation is particularly remarkable in the field of resin-sealing type semi-conductor equipment and the development of durable products for use in a more severe environment has been strongly required.

The above resin-sealing is generally conducted by transfer molding of epoxy resin compositions in view of economy. In particular a system of o-cresol novolak type epoxy resin which a novolak type phenol resin as a hardener is excellent in moisture resistance and hence is mainly employed today.

However, the resin-sealing type semiconductor equipment is being replaced by surface-mounted type semiconductor equipment according to the trend toward the above high density mounting. The surface-mounted type equipment is different from conventional inserted type semi-conductor equipment and the whole package is exposed to a soldering temperature of 200° C. or more. Additionally, in an environment of extended use at high temperatures such as in the periphery of automotive engines, the resin composition used for the sealing material is required to have a high heat-resistance for the severe environment. Conventional epoxy resin cannot fulfil such requirement.

SUMMARY OF THE INVENTION

The object of the present invention is to provide an epoxy resin composition having excellent heat-resistance, particularly an epoxy resin composition which can be applied to the resin-sealing type semiconductor equipment requiring high heat-resistance.

As a result of an intensive investigation in order to improve the heat-resistance of epoxy resins, the present inventors have found that excellent heat-resistance can be obtained by using a compound simultaneously comprising in the molecule a functional group capable of reacting with epoxy resin and a maleimide group having heat-resistance. Thus, the present invention has been completed.

One aspect of the present invention is a heat-resistant epoxy resin composition comprising an epoxy resin, an epoxy hardener, and 2-(4-hydroxyphenyl)-2-(4-maleimidophenyl)propane illustrated by formula (I):

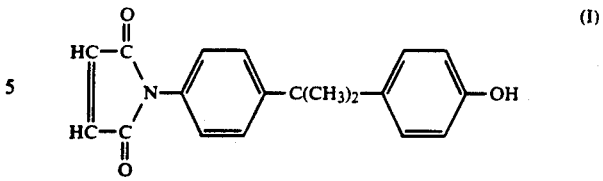

Another aspect of the present invention is a novel process for preparing the compound of formula (I) for use in the composition of the present invention.

The heat-resistant epoxy resin composition of the invention comprising 2-(4-hydroxyphenyl)-2-(4-maleimidophenyl)propane which has a maleimide group can provide high heat-resistance which could not be obtained with a conventional epoxy resin composition. When the resin composition is used for sealing the semiconductor equipment requiring high heat-resistance, excellent reliability can be obtained. Thus, the present invention is valuable in industry.

DESCRIPTION OF THE PREFERRED EMBODIMENTS

Conventional epoxy resins can be employed for the composition of the present invention as long as the epoxy resin is multivalent.

Exemplary epoxy resins which can be used include:
(1) novolak type epoxy resins such as glycidyl derivatives of phenol novolak and cresol novolak:
(2) glycidyl derivatives of other compounds having two or more active hydrogens in a molecule, for example, glycidy) type epoxy resins obtained by reacting polyhydric phenols such as bisphenol A, bis(hydroxyphenyl)methane, resorcinol, bis(hydroxyphenyl)ether, and tetrabromobisphenol A; polyhydric alcohols such as ethylene glycol, neopentyl glycol glycerol, trimethylolpropane, pentaerythritol, diethylene glycol, polypropylene glycol, bisphenol A-ethylene oxide adduct and trihydroxyethylisocyanurate; amino compounds such as ethylenediamine, aniline and bis(4-aminophenyl)-methane; and polycarboxylic acids such as adipic acid, phthalic acid and isophthalic acid; with epichlorohydrin or 2-methylepichlorohydrin, and:
(3) dicyclopentadiene diepoxide and butadiene dimer diepoxide.

One or more epoxy resins selected from the aliphatic and alicyclic epoxy resins such as above may be used.

A preferred epoxy resin is the novolak type epoxy resins such as glycidyl compounds of phenol novolak and cresol novolak in view of heat-resistance and electrical properties in particular.

Resins obtained by modifying the above epoxy resin with silicone oil or silicone rubber can also be used. Such resins include, for example, a silicone modified epoxy resin prepared by the process disclosed in Japanese Patent Laid-Open Publication SHO 62-270617(1987) and 62-273222(1987).

The epoxy hardener used in the composition of the present invention can be any type of epoxy hardener including phenol compounds, amine compounds, acid anhydrides and the like. Phenol compounds are preferred in view of moisture resistance and include, for example, novolak type phenol resins and aralkyl type phenol resins obtained by reacting phenols such as phenol, cresol and resorcinol with aldehydes or aralkyl ethers; and polyhydric phenols such as tri-hydroxyphenylalkanes and tetrahydroxyphenylalkanes. These phenol compounds are used singly or as a mixture.

The amount of the epoxy hardener used is in the range of 0.1 to 10 equivalents, preferably 0.5 to 2 equivalent per equivalents of the epoxy resin.

The composition of the present invention uses 2-(4-hydroxyphenyl)-2-(4-maleimidophenyl)propane, i.e., the compound of formula (I), as a required component.

The compound used can be prepared by known processes. However, a high purity compound can be prepared by a novel process found by the present inventors. The high purity compound can provide a composition which is excellent in heat-resistance and has good and stable quality.

The compound of formula (I) used for the composition of the invention, i.e., 2-(4-hydroxyphenyl)-2-(4-maleimidophenyl)propane is useful as a modifying agent for various polymers. The compound has conventionally been prepared, for example, by reacting 2-(4-hydroxyphenyl)-2-(4-aminophenyl)propane with maleic anhydride in the presence of a large amount of a dehydrating agent such as acetic anhydride, phosphorus oxide or condensed phosphoric acid as disclosed in Japanese Laid-Open Patent Publication SHO 55-149293(1980). However, the process produces acetylated compounds or esterified compounds as by-products because the amine compound used as the raw material has a hydroxyl group. Further, an addition reaction to the double bond of maleimide group takes place and leads to a decrease in the yield and purity and additionally to coloration. Consequently, 2-(4-hydroxyphenyl)-2-(4-maleimidophenyl)propane having good quality could not be obtained.

The novel process described below which has been found by the present inventors has eliminated the disadvantage of the above conventional process and can give a high purity 2-(4-hydroxyphenyl)-2-(4-maleimidophenyl)propane in high yield and without by-products.

That is, the embodiments of the preparation process in the present invention is to prepare the compound in high purity and high yield by conducting a dehydrating and ring-closing reaction of 2-(4-hydroxyphenyl)-2-(4-aminophenyl)propane with maleic anhydride in an organic solvent capable of forming a water azeotrope in the presence of an acid catalyst and an aprotic polar solvent.

The raw materials used in the process are 2-(4-hydroxyphenyl)-2-(4-aminophenyl)propane (hereinafter referred to as amine compound) and maleic anhydride. The amount of maleic anhydride is in the range of 1.0 to 1.5 moles, preferably 1.05 to 1.3 moles per mole of amine compound. When the amount of maleic anhydride is less than 1.0 mole, it sometimes causes formation of unfavorable by-products which are adducts of 2-(4-hydroxyphenyl)-2-(4-maleimidophenyl)propane and excess amine compound remains.

The reaction is carried out in the presence of a catalyst.

Exemplary catalysts which can be used include mineral acids such as sulfuric acid and phosphoric acid, heteropoly acids such as wolframic acid and phosphomolybdic acid, organic sulfonic acids such as p-toluenesulfonic acid and methanesulfonic acid, and halogenated carboxylic acids such as trichloroacetic acid and trifluoroacetic acid. Sulfuric acid and p-toluenesulfonic acid are preferred in particular.

The amount of the catalyst used is usually in the range of 0.5 to 5% by weight per total weight of amine compound and maleic anhydride. A catalyst amount less than 0.5% by weight leads to an insufficient effect of the catalyst. On the other hand, a catalyst amount exceeding 5% by weight is disadvantageous in economy and causes difficulty in removing the residual catalyst.

The reaction is carried out by using solvents. Exemplary solvents used are organic solvents which can remove water by azeotropic distillation. Preferred solvents include, for example, benzene, toluene, xylene, mesitylene and chlorobenzene. The solvent is used in an amount of 3 to 10 times by weight in order to smoothly progress the reaction.

In the process of the invention, an aprotic polar solvent is used in combination with the above organic solvent capable of forming water azeotrope. Exemplary aprotic polar solvents include N,N-dimethylacetamide, N,N-dimethylformamide, N-methyl-2 pyrrolidone, 1,3-dimethyl-2-imidazolidinone and N,N-diethylacetamide. The amount of the aprotic polar solvent is in the range of 10 to 40% by weight, preferably 20 to 30% by weight per weight of the above organic solvent.

The reaction is usually carried out by adding amine compound to the organic solvent solution of maleic anhydride and stirring at 150° C. or less, preferably 20° to 100° C. for 10 minutes or more, preferably 0.5 to 1 hour to form maleamic acid. Successively the aprotic polar solvent and the acid catalyst are added to the reaction mixture obtained, heated to 80° C. or more, preferably to a temperature range of 100° to 180° C., and stirred for 0.5 to 20 hours, preferably 4 to 8 hours to progress the reaction while azeotropically distilling off generated water. Alternatively, a mixture of maleic anhydride, the organic solvent and the catalyst is heated to a temperature range of 80° to 180° C. and a solution of amine compound in the aprotic polar solvent is added dropwise to the mixture. The reaction is progressed while azeotropically removing the generated water.

After completing the reaction by the above steps, the reaction mixture is cooled to 60° to 80° C., and is immediately concentrated under reduced pressure to distill off the solvent. Thereafter water or a mixture of water and a suitable solvent such as methanol, ethanol and isopropyl alcohol is added to obtain 2-(4-hydroxyphenyl)-2-(4-maleimidophenyl)propane.

2-(4-Hydroxyphenyl)-2-(4-maleimidophenyl)propane can be obtained by the process in high purity and high yield as compared with conventionally known processes.

The content of 2-(4-hydroxyphenyl)-2-(4-maleimidophenyl)propane in the composition of the invention is in the range of 10 to 400 parts by weight per 100 parts by weight of the epoxy resin. When the content is less than 10 parts by weight, good resistance to heat cannot be obtained. On the other hand, a content exceeding 400 parts by weight renders the cured product brittle.

Use of curing accelerators in the composition of the invention is desired in order to cure the resin. Curing accelerators which can be used include, for example, imidazoles such as 2-methylimidazole and 2-methyl-4-ethylimidazole; amines such as triethanolamine, triethylenediamine and N-methylmorpholine; organic phosphines such as tributylphosphine, triphenylphosphine and tritolylphosphine; tetraphenylborone salts such as tetraphenylphosphonium tetraphenylborate and triethylammonium tetraphenylborate; and 1,8-diazobicyclo (5,4,0)undecene-7 and derivatives thereof. These curing accelerators may be used singly or as a mixture and, when necessary, may also be used in combination with free-radical initiators such as organic peroxides or azo compounds.

The amount of these curing accelerators used are in the range of 0.01 to 10 parts by weight per 100 parts by weight of the sum of the epoxy hardener and the compound of formula (I).

Other amorphous or crystalline additives may be added to the resin composition in addition to the above components depending upon the use and objects. Representative additives include spherically fused silica powder, alumina powder, silicon nitride powder, silicon carbide powder, glass fibers and other inorganic fillers; release agents such as fatty acids, fatty acid salts and waxes; flame retardants such as bromine compounds, antimony compounds and phosphorus compounds; coloring agents such as carbon black and coupling agents such as silane base, titanate base, and zirco aluminate base.

The present invention will hereinafter be illustrated in detail by way of examples.

EXAMPLE 1

To a reaction vessel equipped with a stirrer, thermometer and an azeotropic distillation trap, 60 g (0.1 mole) of maleic anhydride, 480 g of toluene and 2.6 g of 95% sulfuric acid were charged and heated to a reflux temperature. A solution containing 114 g (0.5 mole) of 2-(4-hydroxyphenyl)-2-(4-aminophenyl)propane in 160 g of N,N'-dimethylacetamide was dropwise added from a dropping funnel over 4 to 5 hours and reacted for 5 hours at the same temperature. Generated water by the reaction was removed by azeotropic distillation. After completing the reaction, the reaction mixture was cooled to 80° to 90° C. and the solvent was successively removed under reduced pressure. The organic layer thus obtained was mixed with 100 ml of isopropyl alcohol and then 300 ml of water was added and stirred for 0.5 to 1 hour to precipitate crystals. The crystals were filtered and dried to obtain 147 g of 2-(4-hydroxyphenyl)-2-(4-maleimidophenyl)propane as yellow crystals. The yield was 96%.

The product had a melting point of 168°-171° C. and a purity of 99% by gel permeation chromatography (GPC).

| | Elemental analysis (%) | | |
|---|---|---|---|
| | C | H | N |
| Calculated | 74.8 | 5.5 | 4.6 |
| Found | 74.1 | 5.66 | 4.5 |
| MS (EI): 307$^{(M+1)}$ | | | |

EXAMPLE 2

The same procedures as conducted in Example 1 were carried out except that 480 g of chlorobenzene was used in place of toluene to obtain 149 g 2-(4-hydroxyphenyl)-2-(4-maleimidophenyl)propane as yellow crystals. The yield was 97%. The product had a melting point of 167° to 171° C. and a purity of 98.5% by GPC.

EXAMPLE 3

The same procedures as conducted in Example 1 were carried out except that 2.6 g of methanesulfonic acid was used as the catalyst, 160 g of N-methyl-2-pyrrolidone was used as the aprotic polar solvent, and 60 g (0.61 mole) of maleic anhydride was used. 2-(4-Hydroxyphenyl)-2-(4-maleimidophenyl)propane thus obtained was 147 g. The yield was 96%. The product was yellow crystals and had a melting point of 167°-171° C. and a purity of 98.5% by GPC.

EXAMPLE 4

To a reaction vessel equipped with a stirrer, thermometer and an azeotropic distillation trap, 300 g (0.3 mole) of maleic anhydride and 240 g of toluene were charged and 57 g (0.25 mole) of 2-(4-hydroxyphenyl)-2-(4-aminophenyl)propane was added with stirring. The reaction was carried out for an hour and then 1.3 g of p-toluenesulfonic acid and 80 g of N,N-dimethylacetamide were added. The resulting mixture was heated to reflux temperature and reacted for 10 hours while azeotropically distilling off water generated by the reaction. After completing the reaction, the reaction mixture was cooled to 80°-90° C. and the solvent was successively distilled off under reduced pressure. The residual organic layer was mixed with 100 ml of methanol and then 300 ml of water. The mixture was stirred for 0.5-1 hour to precipitate crystals. The crystals were filtered and dried to obtain 74 g of 2-(4-hydroxyphenyl)-2- 4-maleimidophenyl) propane as yellow crystals. The yield was 96.3%. The product had a melting point of 168°-171° C. and a purity of 99% GPC.

EXAMPLE 5

The same procedures as conducted in Example 4 was carried out except that 240 g of xylene was used as the organic solvent and 40 g of N,N-dimethylformamide was used as the aprotic polar solvent. 2-(4-Hydroxyphenyl)-2-(4-maleimidophenyl)propane thus obtained was 73.3 g. The yield was 95.5%.

The product was yellow crystals and had a melting point of 168°-171° C. and a purity of 99% by GPC.

EXAMPLES 6 AND 7, AND COMPARATIVE EXAMPLES 1

The formulations of Table 1, the raw material amounts of which are illustrated in parts by weight, were melt-kneaded on hot rolls at 100°-130° C. for 3 minutes, cooled, crushed and tabletted to obtain molding compositions.

The following raw materials were used in the formulations of Table 1.

| Epoxy resin | Trademark, EOCN-1027 |
|---|---|
| | A product of Nippon Kayaku Co. Ltd. |
| Novolak phenol resin | Trademark, PN-80 |
| | A product of Nippon Kayaku Co., Ltd. |
| Phenol aralkyl resin | Trademark, MILEX XL-225L |
| | A product of Mitsui Toatsu Chemicals Inc. |
| Fused silica | Trademark, HARIMICK S-CO |
| | A product of Micron Co., Ltd. |
| Silane coupling agent | Trademark, NCU Silicone A-187 |
| | A product of Nippon Unicar Co., Ltd. |

These compositions were transfer molded at 180° C. for 3 minutes under a pressure of 30 kg/cm² to obtain test pieces for measuring physical properties.

Separately, a test element of 10×10 mm in dimension fitted on the four edges with aluminium bonding pad members of 100×100×1μ in dimension and aluminum wiring of 10μ in width which connected these pad members was mounted on the element fitting portion of a lead frame for a flat package. The lead frame and the bonding pad members were connected with gold wires and the above compositions were transfer molded under the same conditions as above. Thus, semiconductor equipment for tests were prepared. These molded specimens for the tests were post cured at 180° C. for 6 hours prior to the test. Results are illustrated in Table 2.

The following test methods were used.

Glass transition temperature: In accordance with TMA method

Flexural strength: In accordance with JIS K-6911

Heat deterioration test at 200° C.: Flexural strength was measured before and after storing the test piece in a constant temperature oven at 200° C. for 1000 hours. Results are illustrated by the retention of flexural strength.

VSP test: The semiconductor equipment for test was allowed to stand at 121° C. for 24 hours under pressure of 2 atmospheres in a pressure cooker tester and immediately immersed in a FLORENATE liquid (Trademark; FC-70, a product of Sumitomo 3M Co., Ltd.) which was previously maintained at 215° C. The numbers of pieces of semiconductor equipment which generated cracks in the packaging resin were counted. The numerator indicates the number of semiconductors which generated cracks. The denominator indicates the total number of semiconductors tested.

High temperature storage test: The semiconductor equipment was allowed to stand at 200° C. for 1000 hours in a constant temperature oven. Thereafter, operating tests was carried out. Results are illustrated by cumulative failure rate of the semiconductor equipment which did not operate in the test.

TABLE 1

| Raw material | Example 6 | Example 7 | Comparative Example 1 |
| --- | --- | --- | --- |
| Epoxy resin (EP = 195)*1 | 100 | 100 | 100 |
| Novolak phenol resin (OH = 106)*2 | 46 | 23 | 54 |
| Phenol aralkyl resin (OH = 174) | — | 38 | — |
| Compound of Example 1 | 25 | 25 | — |
| Fused silica (average particle size 24μ) | 606 | 659 | 546 |
| Triphenylphosphine | 1.4 | 1.5 | 1.2 |
| Silane coupling agent | 4.7 | 5.1 | 4.2 |
| Carnauba wax | 3.5 | 3.8 | 3.2 |
| Carbon black | 2.3 | 2.5 | 2.1 |
| Antimony oxide | 7.8 | 8.5 | 7.0 |

*1 Epoxy value
*2 OH value

TABLE 2

| Property | Example 6 | Example 7 | Comparative Example 1 |
| --- | --- | --- | --- |
| Glass transition temperature (°C.) | 180 | 180 | 160 |
| Flexural strength (kg/cm²) | | | |
| room temperature | 16.0 | 16.0 | 15.0 |
| 215° C. | 3.5 | 3.5 | 1.0 |
| Heat deterioration at 200° C. (Strength retention after 1000 hrs: %) | 80 | 80 | 50 |
| VSP test (Crack generation rate) | 0/20 | 0/20 | 20/20 |
| High temperature storage test (Cumulative failure rate: %) | 0 | 0 | 63 |

What is claimed is:

1. A heat-resistant epoxy resin composition comprising an epoxy resin, an epoxy hardener and 2-(4-hydroxyphenyl)-2-(4-maleimidophenyl)propane wherein said 2-(4-hydroxyphenyl)-2-(4-maleimidophenyl)propane is prepared by a process comprising conducting a dehydrating and ring-closing reaction of 2-(4-hydroxyphenyl)-2-(4-aminophenyl)propane with maleic anhydride in an organic solvent capable of forming a water azeotrope and in the presence of an acid catalyst and an aprotic polar solvent.

2. The heat-resistant epoxy resin composition of claim 1 wherein the epoxy resin is a novolak epoxy resin, a glycidyl epoxy resin, or an aliphatic or alicyclic epoxy resin.

3. The heat-resistant epoxy resin composition of claim 1 wherein the epoxy resin is a novolak epoxy resin.

4. The heat-resistant epoxy resin composition of claim 1 wherein the epoxy hardener is a novolak phenol resin, an aralkyl phenol resin or a polyhydric phenol.

5. The heat-resistant epoxy resin composition of claim 1, wherein the content of the epoxy hardener is in the range of from 0.1 to 10 equivalents per equivalent of the epoxy resin.

6. The heat-resistant epoxy resin composition of claim 1, wherein the content of 2-(4-hydroxyphenyl)-2-(4-maleimidophenyl)propane is from 10 to 400 parts by weight per 100 parts by weight of the epoxy resin.

7. A process for the preparation of 2-(4-hydroxyphenyl)-2-(4-maleimidophenyl)propane comprising conducting a dehydrating and ring-closing reaction of 2-(4-hydroxyphenyl)-2-(4-aminophenyl)propane with maleic anhydride in an organic solvent capable of forming a water azeotrope in the presence of an acid catalyst and an aprotic polar solvent.

8. The process of claim 7 wherein the aprotic polar solvent is N,N-dimethylformamide, N-methyl-2-pyrrolidone, 1,3-dimethyl-2-imidazolidinone or N,N-diethylacetamide.

9. The process of claim 7 wherein the amount of the aprotic polar solvent is from 10 to 40% by weight per weight of the organic solvent.

10. The process of claim 7 comprising the steps of adding 2-(4-hydroxyphenyl)-2-(4-aminophenyl)propane to a mixture of maleic anhydride and an organic solvent capable of forming a water azeotrope, conducting the reaction at a temperature in the range of from 20° to 150° C. to form corresponding maleamic acid, followed by adding an aprotic polar solvent and an acid catalyst to the resulting reaction mixture, and conducting the reaction by heating to a temperature in the range of from 80° to 180° C. while azeotropically removing generated water.

11. The process of claim 7 comprising the steps of heating a mixture of maleic anhydride, the organic solvent capable of forming a water azeotrope and the acid catalyst at a temperature in the range of from 80° to 180° C. and dropwise adding a solution obtained by previously dissolving 2-(4-hydroxyphenyl)-2-(4-aminophenyl)propane in the aprotic polar solvent while azeotropically removing generated water.

12. A heat-resistant epoxy resin composition comprising an epoxy resin, an epoxy resin hardener and 2-(4-hydroxyphenyl)-2-(4-maleimidophenyl)propane having a melting point of 167° to 171° C.

* * * * *